United States Patent [19]
Choudhury et al.

[11] Patent Number: 5,382,241
[45] Date of Patent: Jan. 17, 1995

[54] ADAPTER ASSEMBLY FOR CANNULA HUB SYRINGE

[75] Inventors: Hrishikesh Choudhury, Gurnee; Joseph F. Julian, Libertyville; John C. Tanner, III, Lake Bluff, all of Ill.

[73] Assignee: Abbott Laboratories, Abbott Park, Ill.

[21] Appl. No.: 130,059

[22] Filed: Sep. 30, 1993

[51] Int. Cl.⁶ ............................................. A61M 5/32
[52] U.S. Cl. ....................... 604/192; 604/239; 604/241; 604/263
[58] Field of Search ............... 604/239, 240–243, 604/173, 272, 192, 195, 197, 199, 201, 905, 198, 263, 110, 83; 128/919, 917

[56] References Cited
U.S. PATENT DOCUMENTS

| | | | |
|---|---|---|---|
| 2,626,603 | 1/1953 | Gabriel | 604/242 |
| 3,485,239 | 12/1969 | Vanderbeck | 604/192 |
| 3,768,474 | 10/1973 | Burke et al. | 604/110 |
| 3,822,701 | 7/1974 | Cloyd | 604/192 |
| 4,116,196 | 9/1978 | Kaplan et al. | 604/201 |
| 4,737,144 | 4/1988 | Choksi | 604/198 |
| 4,737,150 | 4/1988 | Baeumle et al. | 604/239 |
| 4,810,248 | 3/1989 | Masters et al. | 604/263 |
| 4,826,491 | 5/1989 | Schramm | 604/198 |
| 4,897,083 | 1/1990 | Martell | 604/263 |
| 4,909,290 | 3/1990 | Coccia | 604/905 |
| 4,932,940 | 6/1990 | Walker et al. | 604/263 |
| 4,943,282 | 7/1990 | Page et al. | 604/263 |
| 4,976,702 | 12/1990 | Andrews et al. | 604/263 |
| 5,046,509 | 9/1991 | Kater | 604/272 |
| 5,135,489 | 8/1992 | Jepson et al. | 604/905 |
| 5,147,324 | 9/1992 | Skakoon et al. | 604/905 |
| 5,151,090 | 9/1992 | Best et al. | 604/263 |
| 5,215,535 | 6/1993 | Gettig et al. | 604/263 |

FOREIGN PATENT DOCUMENTS 0556482  4/1958  Canada ............... 604/241

Primary Examiner—C. Fred Rosenbaum
Assistant Examiner—Mark Bockelman
Attorney, Agent, or Firm—A. Nicholas Trausch

[57] ABSTRACT

A multiple configuration adapter assembly is provided for a prefilled emergency syringe and includes a cylindrical sheath, a removable sharp needle assembly and a luer extension assembly.

5 Claims, 2 Drawing Sheets

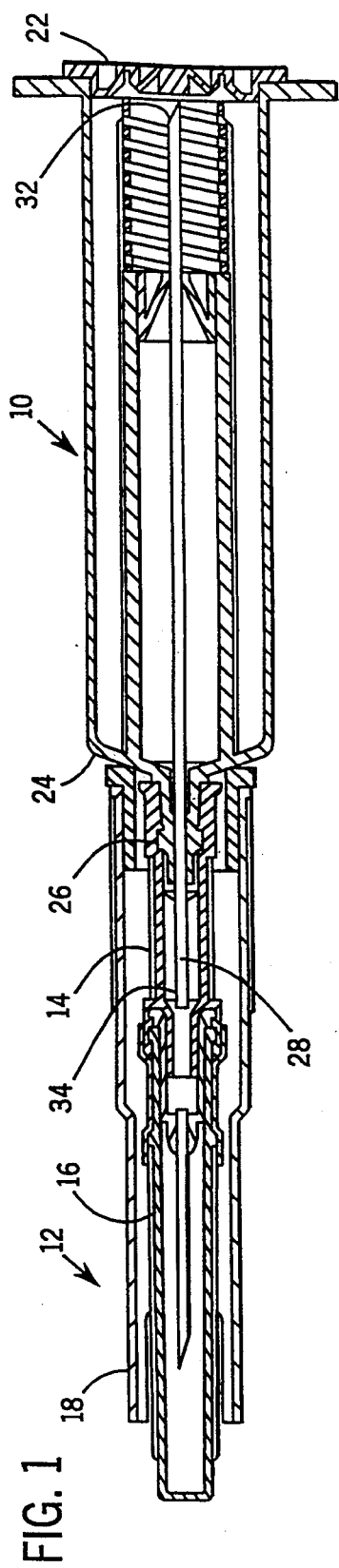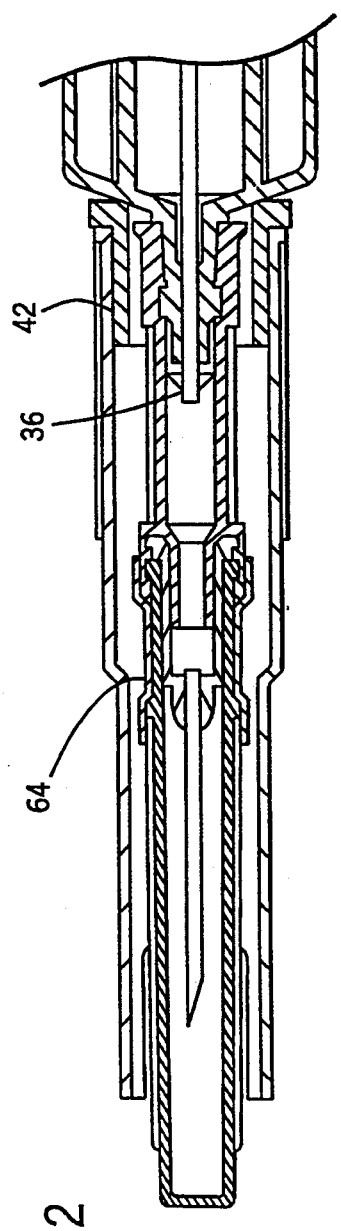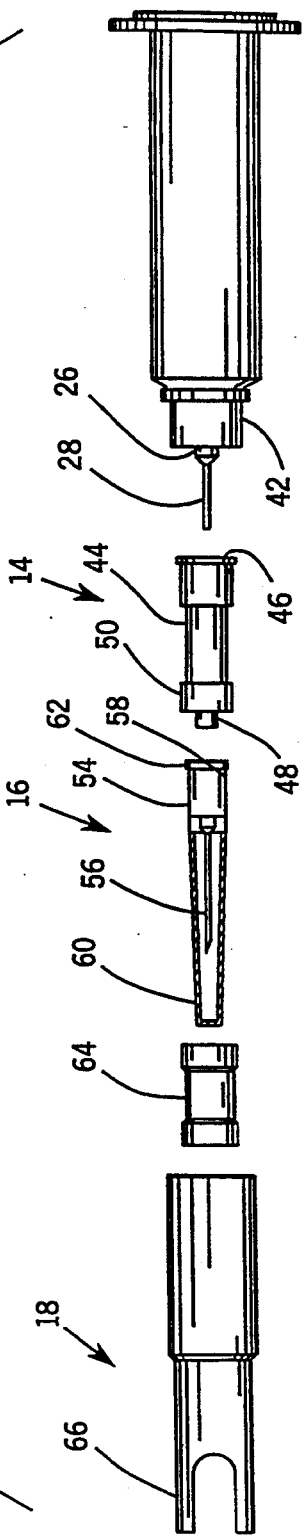

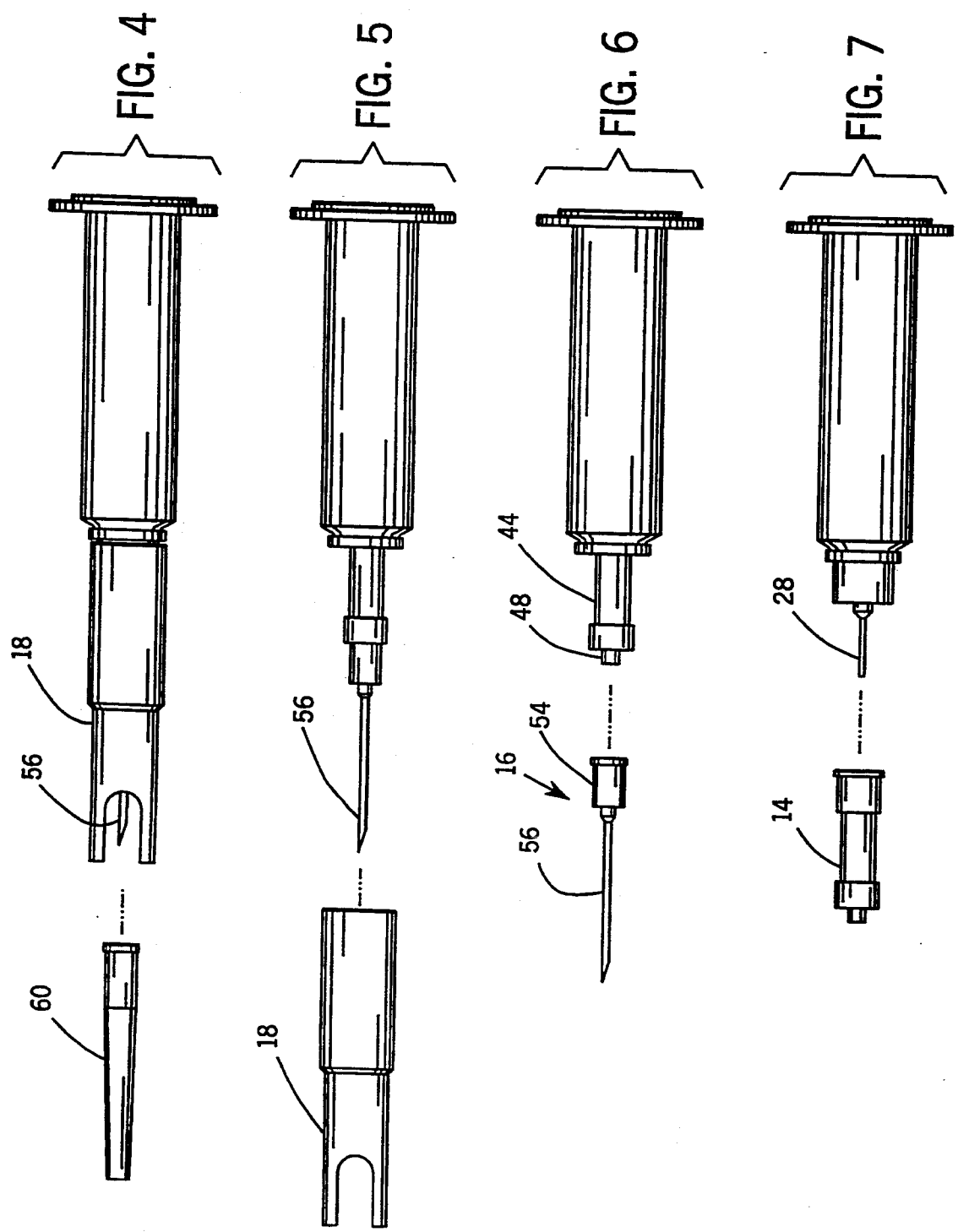

ADAPTER ASSEMBLY FOR CANNULA HUB SYRINGE

FIELD OF THE INVENTION

The present invention relates to a prefilled unit of use syringe and in particular to a syringe housing of the type having a blunt cannula extending from an integral hub and a removable multiple configuration adapter assembly including a guarded sharp needle, a sharp needle, and a luer connection.

BACKGROUND OF THE INVENTION

Prefilled syringes, such as the Abboject ® Unit of Use Emergency Syringe sold by Abbott Laboratories, are used for both direct and indirect injections into a patient. For example, the sharp needle can be used for hypodermic injections directly through the patient's skin. The same sharp needle can be used for infusions into a standard reseal on an intravenous administration tubing set having a venous access catheter to the patient.

The Abboject Syringe system includes a calibrated glass vial prefilled with a medical solution and a mating vial injector. The vial injector (or syringe housing) traditionally includes an integral, forward extending sharp delivery needle that can be used to inject the medical solution directly into a patient or into a reseal on an I.V. administration set connected to a patient. The traditional Abboject syringe is assembled with the delivery needle enclosed by a removable needle cover to protect against accidental needle stick prior to use. The cover also protects the sterile needle from contamination prior to use.

Patients and healthcare workers are sensitive to the danger of accidental needle stick from exposed sharp needles. Blood borne diseases such as AIDS and hepatitis can be transmitted by accidental needle sticks from sharp needles previously in contact with an infected patient's blood system.

Currently there are many efforts to reduce the number of exposed sharp needles in the healthcare environment, especially in emergency situations. The efforts include making one initial venous entry with a catheter into the patient's blood system and then providing a connecting I.V. administration set with reusable and/or multiple access sites. This procedure minimizes the need for direct injections and potential contact with the patient's blood system. Another effort is to provide removable and/or permanent needle guards such as the Lifeshield ® Abboject ® Emergency Syringe with Needle Guard, sold by Abbott Laboratories. These guarded needle syringes are used in place of unguarded needles when sharp needle syringes are absolutely necessary. Further efforts include using blunt cannula with prepierced reseals for I.V. connections rather than traditional sharp needles and pierceable reseals. Alternatively, luer fitment connections are used in I.V. set connections in place of sharp needles and reseals.

In addition to emergency syringes, prefilled syringes are used for routine procedures such as therapeutic drug administration. This casual use may expose the healthcare worker to an additional type of accidental needle stick. Besides a life-threatening blood infection that may have infiltrated from the patient's blood system, the worker may be exposed to the side effects of drug residual in the needle, such as an oncology drug.

An example of a protective sheath and cap for a syringe needle is shown in U.S. Pat. No. 4,232,669 to Nitshke. The syringe is intended for use with an additive port of a flexible bag and therefore the sheath does not extend beyond the needle point. The sheath and a removable protective cap maintains the sterility of the syringe needle. However, the health care worker is at risk of accidental needle stick when the protective cap is removed. The sheath of Nitshke is attached to the syringe by an collar engaging the needle hub. Therefore a protective sheath similar to the sheath suggested by Nitshke could not be added to the standard Abboject Syringe without extensively redesigning the syringe and the syringe manufacturing process. The needle hub of the current Abboject Syringe is already used as a friction fit for the needle hood.

A protected needle is also disclosed in U.S. Pat. No. 4,834,716 to Ogle. In FIG. 2 of Ogle, the protective sheath is fixed to the needle hub of the syringe. As previously discussed, fixing a protective sheath to the needle hub as suggested by Ogle does not allow a needle hood to be attached to the hub of the standard Abboject syringe as currently manufactured.

Since the Abboject Syringe system has many uses in the healthcare field, any changes to the syringe configuration must not prevent or encumber the various uses, but should enhance the syringe's safe use.

Therefore it is desirable to provide a prefilled syringe system that decreases the risk of accidental needle stick yet is readily adaptable to the various configurations for use in the different infusion and/or connection procedures currently needed in a healthcare facility, such as a guarded needle, a sharp needle, a luer connection, or a blunt cannula connection.

Furthermore, it is desirable that the protection and safety features are compatible with the standard prefilled syringes currently manufactured and in the healthcare inventory. For example, any new syringe configuration should continue to be compatible and interchangeable in use with the Lifeshield Abboject Syringe with Guarded Needle for connection to resealable access sites on I.V. sets. Compatibility is desired so as to providing continuity, economy and flexibility in managing syringe inventory and costs by the healthcare institutions.

It is desirable to provide a prefilled syringe for use as a guarded sharp needle syringe, as an unguarded sharp needle syringe, as a luer connection syringe and as a blunt cannula syringe.

It is desirable that the various connection and needle components be already assembled to the prefilled syringe so that the syringe is ready for use without having to add components during an emergency procedure. Rather, the adapter assembly should provide components that are preassembled and easily removed if not needed.

It is desirable that the health care worker can make either a guarded needle connection or an unguarded needle connection by only having to remove a selected cover element.

It is therefore a primary object of the present invention to provide a multiple use adapter assembly for the Abboject Syringe system so as to facilitate easy use in an emergency situation and to protect the healthcare provider from accidental needle stick.

It is another object of the present invention to add the multiple use adapter assembly to presently manufactured Abboject Syringes so that the adapted syringes may be used interchangeable with the current connection devices in use.

It is another object of the present invention to protect the sterile sharp needle, the luer adapter fitment, and the blunt cannula connection from contamination prior to use.

It is another object of the present invention to provide easy and safe conversion of a prefilled syringe and especially an emergency syringe to the desired connection configuration.

SUMMARY OF THE INVENTION

The present invention is directed to a prefilled blunt cannula syringe that includes a removable needle guard, a sharp needle assembly, and a luer adapter assembly.

The preferred embodiment of the invention includes a multiple configuration adapter assembly that can be completely or modularly (i.e. partially) removed. The adapter assembly is used with a standard injector housing for a prefilled syringe of the type having a closed front wall of the syringe housing and a coaxially extending blunt cannula. An annular clearance space is maintained adjacent to the cannula hub for the adapter assembly to be removably assembled on the hub.

More particularly the removable adapter assembly includes a hollow, cylindrical tube which fits over and extends beyond the terminal end of the blunt cannula. A luer fitment at the proximal end of the tubular adapter is removably attachable to the tapered cannula hub. The tubular adapter also includes a male luer fitment at the distal end of the tube and a securing mechanism, such as a threaded circumferential flange, surrounding the distal luer fitment. A removable sharp needle and cover assembly is removably attached to the luer fitment and rotationally secured to the securing mechanism.

A predominately axial force applied to the extending needle cover in the axial direction removes the needle cover, exposing the sharp needle. A rotational force applied to the sharp needle assembly in a predetermined direction removes the sharp needle assembly from the securing mechanism, exposing a luer fitment. An axial force applied to the hollow tube assembly in the axial direction removes the hollow tube assembly and the attached needle assembly, exposing the blunt cannula.

A hollow protective, sheath is also removable attached to an annular flange on the closed end of the injector housing. The open end of the protective sheath extends beyond the sharp point of the sharp needle assembly. The needle cover extends beyond the open end of the sheath. With the protective sheath attached, a predominately axial force applied to the extending needle cover, as set forth above, removes the needle cover while the uncovered sharp needle is guarded by the protective sheath so as to reduce the chance of accidental needle stick by the exposed sharp needle.

Other advantages and features of the present invention will become apparent from the following detailed description, the accompanying drawings and the appended claims.

BRIEF DESCRIPTION OF THE DRAWINGS

FIG. 1 is a cross section of the preferred embodiment of the present invention showing an emergency syringe injector housing having an integral blunt cannula and an axially extending hub, a concentrically attached annular flange, a removable hollow protective sheath, a removable luer adapter, and a removable sharp needle assembly;

FIG. 2 is an enlarged side view in section of an assembled emergency syringe system according to an alternative embodiment of the present invention;

FIG. 3 is an exploded side view partially in section of FIG. 1 showing the hollow sheath, the sharp needle and cover assembly, and the luer extension prior to attachment to the syringe injector housing;

FIG. 4 is a side view of the syringe injector system according to the present invention that is configured in the protected needle mode for use with a reseal connector;

FIG. 5 is a side view of the syringe injector system according to the present invention that is configured in the sharp needle mode for use as a hypodermic syringe;

FIG. 6 is a side view of the syringe injector system according to the present invention that is configured for use with a standard luer fitment connector; and FIG. 7 is a side view of the syringe injector system according to the present invention that is configured in the blunt cannula mode.

DETAILED DESCRIPTION OF THE PREFERRED EMBODIMENT

Co-pending U.S. patent application Ser. No. 08/055,058 now pending, titled "Needle Guard Assembly for Syringe" filed Apr. 29, 1993 as a Continuation Application of U.S. patent application Ser. No. 07/765,356, filed Sep. 25, 1991 and now abandoned, and co-pending U.S. patent application Ser. No. 08/031,789 filed Mar. 15, 1993 now U.S. Pat. No. 5,322,515 and titled "Luer Adapter Assembly for Emergency Syringe" are hereby incorporated by reference in this application. As indicated by their titles, these incorporated pending patent applications cover a first generation prefilled syringe with a permanent guarded needle and a second generation syringe having a guarded needle and luer adapter. These two patent applications describe adapter configurations that address only part of the proposed needle stick reduction. The present invention as described and claimed herein addresses additional configurations.

FIGS. 1 shows a cross section of a complete syringe injector housing 10 and a preferred embodiment of the removable multiple configuration adapter assembly 12 of the present invention. The adapter assembly 12 includes a removable luer extension 14, a removable sharp needle and cover assembly 16, and a removable protective sheath 18. The construction and use of these modular subassemblies will be further described below.

The syringe injector housing 10 is an elongated, rigid, and hollow cylinder typically constructed of a moldable thermoplastic such as a medical grade polypropylene. The hollow injector housing 10 is open at the rear end. A removable cap 22 closes the rear end of the housing until the prefilled glass vial (not shown) is matingly attached.

Front wall portion 24 substantially closes the front end of the syringe injector housing. An integrally molded cannula hub 26 extends forward from the front wall and integrally secures a cannula 28 within the syringe housing. The forward extending cannula hub 26 has a luer taper on the outside surface. The cannula 28 also extends rearward within the housing and terminates with a sharp rear point 32 at the distal end of the injector housing.

The prefilled glass vial (not shown) is separately manufactured and filled with one of many suitable medical solutions. The filled vial is sealed with a slidable elastomeric stopper and sterilized. An appropriate number of injector housings plus a larger number of solution vials are stored or inventoried in a hospital pharmacy, in a transportable emergency kit, or other places of use. When a specific medical solution in a vial is selected for injection or infusion, the vial stopper is threadingly engaged with the rear end of the syringe injector housing 10. The stopper is pierced by the rear point 32 of the cannula so as to provide fluid communication to the forward end of the cannula 28.

A portion of the integral syringe housing cannula 28 extends forward beyond the cannula hub 26. As shown in the preferred embodiment of FIG. 1, the forward extending portion of the cannula 28 is extended sufficiently beyond the cannula hub to form a blunt cannula connector 34 for fluid connection with pre-pierced reseals currently in use such as the Lifeshield ® Pre-pierced Reseal sold by Abbott Laboratories. In another embodiment of the invention, depicted in FIG. 2, the cannula 28 is minimally extended forward to a blunt delivery point 36 and may not be of sufficient length to use the cannula as a connector with pre-pierced reseals.

Referring now to FIGS. 1-3, a short, axially extending annular plastic flange 42 is permanently attached to the front wall portion 24 of the syringe housing by one of various joining techniques such as spin welding, solvent bonding or ultrasonic welding. The flange 42 is preferably separately molded of the same material as the syringe housing 10 or alternately can be integrally molded with the syringe housing. The flange 42 coaxially extends forward with the cannula hub 26 but does not extend beyond the tapered hub 26. The annular flange 42 is positioned on the front wall 24 of the syringe housing with a predetermined radial clearance between the outer diameter of the hub 26 and the interior diameter of the flange wall 42.

The removable luer extension component 14 includes a small diameter, hollow tube 44 preferably molded of a rigid plastic such as a medical grade polycarbonate and having an axial fluid passageway therethrough. An internal female luer fitment 46 is provided at the proximal end of the tube. An external male luer tapered portion 48 is integrally formed at the distal end of the tube. A securing mechanism such as a circumferential flange having internal threads 50 is positioned around the external luer fitment 48. The internal luer taper 46 at the proximal end of the luer extension component 14 is removably engaged with the tapered cannula hub 26 of the syringe housing to sealingly extend fluid communication from the syringe cannula 28 to the external luer fitment 48 of the extension 14.

The adapter assembly 12 also includes a removable sharp needle and cover assembly 16. The needle portion includes a tapered hub 54 having a permanently secured, forward extending sharp needle 56. An interior male luer fitment 58 is provided on the interior surface of the tapered hub 54. A tubular needle cover 60 encloses the sharp needle 56 and is removably engaged to the outside tapered hub 54 of the needle. Small radially extending lugs 62 at the proximal end of hub 54 permit the sharp needle assembly 16 to be rotationally secured to the threaded securing mechanism 50 of the luer extension 14. Additionally a shrink wrap band 64 provides a sterile barier at the removable connection between the luer extension 14 and the sharp needle assembly 16.

The hollow protective sheath 18 is a separately molded hollow cylinder having a tapered interior diameter. The interior dimension of the sheath 18 is sized to accommodate the axially unobstructed removal of the needle cover 60 from the sharp needle 56. The axially unobstructed clearance space allows the needle cover 60 to be readily removed from the needle hub 54 so as to expose the sharp needle 56 within the sheath 18. The distal end opening 66 of the sheath is of sufficient radial size to provide clearance to the outer diameter of a reseal when the sheath 18 and uncovered sharp needle 56 are inserted onto a reseal so as to fluidly engage the reseal.

The proximal end of the luer extension 14 is sized to unobstructively occupy the annular clearance space that is maintained between the needle hub 26 and the interior of the annular flange 42. The clearance space allows the internal luer taper 46 of the extension 14 to be removably attached to the hub 26. The sheath 18 is removably attached, such as by a slip fit to the exterior of the annular flange 42 on the injector housing.

The forward open end 66 of the sheath extends longitudinally forward beyond the sharp needle 56. Optionally, cut-outs are provided to assist in coupling to Y-site type connections.

The manufacture of the above described multiple configuration syringe will now be described. The current manufacturing process for an Abboject emergency syringe includes (or can readily be modified to include) the manufacture of a syringe housing 10 having a blunt cannula 28 extending from a tapered hub 26. A luer adapter tube 44 is fitted over the extending cannula 28 and onto the tapered cannula hub 26. A preassembled sharp needle assembly 16, including the needle cover 60 is attached to the luer fitment 48 at the distal end of the luer extension tube 44. The connection is secured by threading the radial lugs 62 into the internal circumferential threads 50 on the luer extension tube. The connection is further sealed by shrink wrap 64 that seals the juncture.

An alternate assembly sequence includes assembling the preassembled sharp needle assembly 16 to the luer extension assembly 14 and applying the shrink band 64 prior to attaching the luer extension 14 to the syringe housing 10. Lastly the protective sheath 18 is slip fit onto the flange 42 previously attached to the syringe housing.

Each of the alternatively assembled configurations described above requires a clearance space between the cannula hub 26 and the interior of the cylindrical sheath 18 for the luer adapter assembly 14.

The adapter assembly 12 permits the Abboject syringe of the present invention to be packaged in a conventional package and sterilized in a conventional manner, such as by radiation sterilization. The interior of the sheath 18 does not need to be maintained sterile. Therefore a closure is not needed to cover the open end 66 of the sheath. Furthermore, since the sheath interior does not need to be maintained sterile, the connection between the base of the sheath 18 and the annular flange 42 on the front wall 24 of the injector housing does not need to be sealed. The connection only needs to provide a strong and solid anchor for the protective sheath 18 to reduce accidental needle stick.

It will be apparent from the foregoing description that the multiple configuration adapter assembly of the present invention not only protects the healthcare provider from inadvertent or accidental needle stick, but also provides additional advantages.

Any desired configuration of the syringe can be achieved in two or fewer steps. Referring now to FIGS.

4–7, the multiple configurations will be described. In FIG. 4, the needle cover 60 is removed by an axial pulling force to achieve a guarded needle configuration.

In FIG. 5, the protective sheath 18 is removed, preferably first, and then the needle cover 60 (not shown) to achieve the sharp needle configuration.

In FIG. 6, the protective sheath 18 is removed first. Then the sharp needle assembly 16 (including the still intact needle cover 60 and shrink band 64, not shown) is removed by applying a rotational force to the sharp needle assembly 16 to achieve the luer connection configuration.

In FIG. 7, the protective sheath 18 is removed first and then the combined sharp needle assembly 16 and luer extension assembly 14 is removed by applying an axial force to achieve the blunt cannula configuration.

Although the present invention has been disclosed in terms of a preferred embodiment, it will be apparent to those skilled in the art that variations and modifications can be made without departing from the spirit and scope of the invention as defined in the following claims.

We claim:

1. A syringe assembly having a cylindrical, closed-end injector housing portion, a tapered cannula hub circumferentially extending from the closed end of the injector housing portion, a blunt cannula extending from the tapered cannula hub, and an adapter assembly removably attached to the tapered cannula hub, the adaptor assembly comprising:

an axially extending hollow tube having a proximal end, a distal end, and a length greater than the extending blunt cannula;

a first interior luer fitment at the proximal end of the hollow tube, the first luer fitment removably attached in an axial manner to the tapered cannula hub;

an exterior luer taper portion and first securing means at the distal end of the hollow tube; and a removable sharp needle assembly including:

a tapered needle hub having a second interior luer fitment and second securing means, the second interior luer fitment removably attached to the exterior luer taper portion and the second securing means removably secured in a rotational manner to the first securing means at the distal end of the hollow tube, a sharp needle extending from the tapered needle hub, and a tubular needle cover removably attached in an axial manner to the tapered needle hub to surround the sharp needle, so that a predominantly axial force applied to the needle cover removes the needle cover from the tapered needle hub, and so that a rotational force applied to the removable sharp needle assembly removes the sharp needle assembly and second securing means from the distal end of the hollow tube and the first securing means, and so that an axial force applied to the hollow tube in an axial direction removes the hollow tube and attached sharp needle assembly from the tapered cannula hub; and an annular flange fixed to the closed end of the injector so that the flange does not extend beyond the tapered cannula hub and a hollow sheath having a first and second open end, the first open end slidably and removable attached to the annular flange at the closed end of the injector housing portion so that the adapter assembly fits within the inner diameter of the sheath and only the tubular needle cover extends beyond the second open end of the of the sheath.

2. The luer adapter assembly of claim 1 wherein the first open end of the sheath has two oppositely disposed cutouts.

3. The syringe assembly of claim 1 wherein the first securing means is an interior threaded extension circumferentially surrounding the luer fitment.

4. The syringe of claim 3 wherein the rotational force applied to the removable sharp needle assembly is a torque in the opposite direction of the threads of the threaded extension.

5. The adapter assembly of claim 1 wherein the tapered cannula hub is an external luer taper.

* * * * *